(12) United States Patent
Zemlok (10) Patent No.: US 11,832,813 B2
(45) Date of Patent: *Dec. 5, 2023

(54) POWERED SURGICAL INSTRUMENT

(71) Applicant: Covidien LP, Mansfield, MA (US)

(72) Inventor: Michael A. Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/961,756

(22) Filed: Oct. 7, 2022

(65) Prior Publication Data

US 2023/0040311 A1 Feb. 9, 2023

Related U.S. Application Data

(63) Continuation of application No. 17/064,638, filed on Oct. 7, 2020, now Pat. No. 11,464,509, which is a
(Continued)

(51) Int. Cl.
*A61B 17/068* (2006.01)
*A61B 17/072* (2006.01)
(Continued)

(52) U.S. Cl.
CPC ...... *A61B 17/068* (2013.01); *A61B 17/00234* (2013.01); *A61B 17/07207* (2013.01);
(Continued)

(58) Field of Classification Search
CPC ............ A61B 17/068; A61B 17/00234; A61B 17/07207; A61B 2017/00022;
(Continued)

(56) References Cited

U.S. PATENT DOCUMENTS

| 37,165 A | 12/1862 | Gary |
| 2,675,003 A | 4/1954 | Veley |

(Continued)

FOREIGN PATENT DOCUMENTS

| EP | 0647431 A2 | 4/1995 |
| EP | 0738501 A1 | 10/1996 |

(Continued)

OTHER PUBLICATIONS

European Search Report dated Apr. 17, 2007 for Corresponding Patent Application EP06026840.
(Continued)

*Primary Examiner* — Dariush Seif
(74) *Attorney, Agent, or Firm* — CARTER, DELUCA & FARRELL LLP (57) ABSTRACT

A surgical instrument including a housing, an endoscopic portion, a drive motor, a drive tube, a firing rod and an end effector is disclosed. The endoscopic portion extends distally from the housing and defines a first longitudinal axis. The drive motor is disposed at least partially within the housing. The drive tube is disposed in mechanical cooperation with the drive motor and is rotatable about a drive tube axis extending through the drive tube. The firing rod is disposed in mechanical cooperation with the drive tube and at least a portion of the firing rod is translatable with respect to the drive tube. The end effector is disposed adjacent a distal portion of the endoscopic portion and is in mechanical cooperation with the firing rod so that the firing rod drives a surgical function of the end effector.

20 Claims, 8 Drawing Sheets

Related U.S. Application Data continuation of application No. 15/695,824, filed on Sep. 5, 2017, now Pat. No. 10,799,238, which is a continuation of application No. 14/452,782, filed on Aug. 6, 2014, now abandoned, which is a continuation of application No. 11/786,933, filed on Apr. 13, 2007, now Pat. No. 8,800,837.

(51) Int. Cl.
  *A61B 17/00* (2006.01)
  *A61B 17/29* (2006.01)
(52) U.S. Cl.
  CPC ............ *A61B 2017/00022* (2013.01); *A61B 2017/00398* (2013.01); *A61B 2017/00734* (2013.01); *A61B 2017/2901* (2013.01); *A61B 2017/2927* (2013.01)
(58) Field of Classification Search
  CPC ......... A61B 2017/00398; A61B 2017/00734; A61B 2017/2901; A61B 2017/2927
  USPC ............................................ 227/175.1–182.1
  See application file for complete search history.

(56) References Cited

U.S. PATENT DOCUMENTS

| | | |
|---|---|---|
| 3,079,606 A | 3/1963 | Bobrov et al. |
| 3,209,754 A | 10/1965 | Brown |
| 3,273,562 A | 9/1966 | Brown |
| 3,490,675 A | 1/1970 | Green et al. |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,212,297 A * | 7/1980 | Frosch ............. A61M 16/0465 128/207.14 |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A * | 12/1984 | Swiggett ............. A61B 17/115 227/179.1 |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,573,468 A * | 3/1986 | Conta ................. A61B 17/115 227/179.1 |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,648,541 A * | 3/1987 | Mongeon ........... A61B 17/0682 227/19 |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,007 A * | 11/1993 | Spetzler ............. A61B 17/1285 606/208 |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Suruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,569,270 A * | 10/1996 | Weng ................. A61B 17/0469 606/147 |
| 5,571,116 A | 11/1996 | Bolanos et al. |

(56) References Cited

U.S. PATENT DOCUMENTS

| | | |
|---|---|---|
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,628,446 A * | 5/1997 | Geiste ............... A61B 17/0684 227/176.1 |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,692,668 A | 12/1997 | Schulze et al. |
| 5,693,042 A | 12/1997 | Boiarski et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,752,644 A | 5/1998 | Bolanos et al. |
| 5,755,726 A | 5/1998 | Pratt et al. |
| 5,759,171 A | 6/1998 | Coelho et al. |
| 5,779,130 A | 7/1998 | Alesi et al. |
| 5,782,397 A * | 7/1998 | Koukline ............ A61B 17/0686 227/176.1 |
| 5,785,713 A | 7/1998 | Jobe |
| 5,788,698 A | 8/1998 | Savornin |
| 5,792,165 A * | 8/1998 | Klieman ............... A61B 34/71 606/174 |
| 5,810,811 A | 9/1998 | Yates et al. |
| 5,817,119 A * | 10/1998 | Klieman ............... A61B 17/29 606/174 |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,868,685 A | 2/1999 | Powell et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,120,462 A * | 9/2000 | Hibner ............... A61B 10/0275 600/568 |
| 6,123,702 A | 9/2000 | Swanson et al. |
| 6,126,058 A | 10/2000 | Adams et al. |
| 6,126,651 A * | 10/2000 | Mayer ................. A61B 34/70 606/1 |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,220,368 B1 * | 4/2001 | Ark ................... A61B 17/1626 173/217 |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| 6,412,279 B1 | 7/2002 | Coleman et al. |

(56) References Cited

U.S. PATENT DOCUMENTS

| | | | |
|---|---|---|---|
| 6,425,903 B1 | 7/2002 | Voegele | |
| 6,436,097 B1 | 8/2002 | Nardella | |
| 6,436,107 B1 | 8/2002 | Wang et al. | |
| 6,436,110 B2 | 8/2002 | Bowman et al. | |
| 6,443,973 B1 | 9/2002 | Whitman | |
| 6,447,517 B1 | 9/2002 | Bowman | |
| 6,461,372 B1 | 10/2002 | Jensen et al. | |
| 6,478,210 B2 | 11/2002 | Adams et al. | |
| 6,497,707 B1 | 12/2002 | Bowman et al. | |
| 6,505,768 B2 | 1/2003 | Whitman | |
| 6,515,273 B2 | 2/2003 | Al-Ali | |
| 6,517,565 B1 | 2/2003 | Whitman et al. | |
| 6,524,316 B1 | 2/2003 | Nicholson et al. | |
| 6,533,157 B1 | 3/2003 | Whitman | |
| 6,540,751 B2 | 4/2003 | Enayati | |
| 6,544,273 B1 | 4/2003 | Harari et al. | |
| 6,554,852 B1 | 4/2003 | Oberlander | |
| 6,562,071 B2 | 5/2003 | Jarvinen | |
| 6,578,579 B2 | 6/2003 | Burnside et al. | |
| 6,601,748 B1 | 8/2003 | Fung et al. | |
| 6,601,749 B2 | 8/2003 | Sullivan et al. | |
| 6,602,252 B2 | 8/2003 | Mollenauer | |
| 6,611,793 B1 | 8/2003 | Burnside et al. | |
| 6,616,821 B2 | 9/2003 | Broadley et al. | |
| 6,629,986 B1 | 10/2003 | Ross et al. | |
| 6,651,669 B1 | 11/2003 | Burnside | |
| 6,656,177 B2 | 12/2003 | Truckai et al. | |
| 6,669,073 B2 | 12/2003 | Milliman et al. | |
| 6,669,705 B2 | 12/2003 | Westhaver et al. | |
| 6,696,008 B2 | 2/2004 | Brandinger | |
| 6,698,643 B2 | 3/2004 | Whitman | |
| 6,699,177 B1 | 3/2004 | Wang et al. | |
| 6,716,233 B1 | 4/2004 | Whitman | |
| 6,736,085 B1 | 5/2004 | Esnouf | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,843,403 B2 | 1/2005 | Whitman | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,861,639 B2 | 3/2005 | Al-Ali | |
| 6,872,214 B2 | 3/2005 | Sonnenschein et al. | |
| 6,899,538 B2 | 5/2005 | Matoba | |
| 6,900,004 B2 | 5/2005 | Satake | |
| 6,905,057 B2 | 6/2005 | Swayze et al. | |
| 6,926,636 B2 | 8/2005 | Luper | |
| 6,953,139 B2* | 10/2005 | Milliman | A61B 17/07207 227/19 |
| 6,959,852 B2* | 11/2005 | Shelton, IV | A61B 17/07207 227/19 |
| 6,979,328 B2 | 12/2005 | Baerveldt et al. | |
| 6,981,628 B2* | 1/2006 | Wales | A61B 17/07207 227/180.1 |
| 6,981,941 B2 | 1/2006 | Whitman et al. | |
| 6,988,649 B2 | 1/2006 | Shelton, IV et al. | |
| 7,000,819 B2 | 2/2006 | Swayze et al. | |
| 7,032,798 B2 | 4/2006 | Whitman et al. | |
| 7,044,353 B2* | 5/2006 | Mastri | A61B 17/07207 227/176.1 |
| 7,048,687 B1 | 5/2006 | Reuss et al. | |
| 7,059,508 B2 | 6/2006 | Shelton, IV et al. | |
| 7,077,856 B2 | 7/2006 | Whitman | |
| 7,083,075 B2 | 8/2006 | Swayze et al. | |
| 7,097,089 B2 | 8/2006 | Marczyk | |
| 7,111,769 B2 | 9/2006 | Wales et al. | |
| 7,118,564 B2 | 10/2006 | Ritchie et al. | |
| 7,122,029 B2 | 10/2006 | Koop et al. | |
| 7,128,253 B2 | 10/2006 | Mastri et al. | |
| 7,128,254 B2 | 10/2006 | Shelton, IV et al. | |
| 7,140,528 B2 | 11/2006 | Shelton, IV | |
| 7,143,924 B2 | 12/2006 | Scirica et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,186,966 B2 | 3/2007 | Ai-Ali | |
| 7,193,519 B2 | 3/2007 | Root et al. | |
| 7,217,269 B2 | 5/2007 | El-Galley et al. | |
| 7,220,232 B2 | 5/2007 | Suorsa et al. | |
| 7,225,963 B2 | 6/2007 | Scirica | |
| 7,240,817 B2 | 7/2007 | Higuchi | |
| 7,241,270 B2 | 7/2007 | Horzewski et al. | |
| 7,246,734 B2 | 7/2007 | Shelton, IV | |
| 7,303,108 B2* | 12/2007 | Shelton, IV | A61B 17/0682 227/176.1 |
| 7,328,828 B2 | 2/2008 | Ortiz et al. | |
| 7,335,169 B2 | 2/2008 | Thompson et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,422,136 B1* | 9/2008 | Marczyk | A61B 17/07207 227/176.1 |
| 7,431,188 B1 | 10/2008 | Marczyk | |
| 7,461,767 B2 | 12/2008 | Viola et al. | |
| 7,464,846 B2 | 12/2008 | Shelton, IV et al. | |
| 7,464,847 B2 | 12/2008 | Viola et al. | |
| 7,481,347 B2 | 1/2009 | Roy | |
| 7,494,039 B2 | 2/2009 | Racenet et al. | |
| 7,506,790 B2 | 3/2009 | Shelton, IV | |
| 7,556,185 B2 | 7/2009 | Viola | |
| 7,950,560 B2 | 5/2011 | Zemlok et al. | |
| 8,800,837 B2* | 8/2014 | Zemlok | A61B 17/07207 227/176.1 |
| 10,799,238 B2 | 10/2020 | Zemlok | |
| 11,464,509 B2 | 10/2022 | Zemlok | |
| 2002/0025891 A1 | 2/2002 | Colosky et al. | |
| 2002/0103489 A1 | 8/2002 | Ku | |
| 2002/0111641 A1 | 8/2002 | Peterson et al. | |
| 2002/0165541 A1 | 11/2002 | Whitman | |
| 2003/0009195 A1 | 1/2003 | Field et al. | |
| 2003/0073981 A1 | 4/2003 | Whitman et al. | |
| 2003/0114851 A1 | 6/2003 | Truckai et al. | |
| 2003/0120306 A1 | 6/2003 | Burbank et al. | |
| 2003/0139746 A1 | 7/2003 | Groiso | |
| 2004/0094597 A1 | 5/2004 | Whitman et al. | |
| 2004/0232199 A1 | 11/2004 | Shelton et al. | |
| 2004/0232201 A1* | 11/2004 | Wenchell | A61B 17/07207 227/176.1 |
| 2004/0249366 A1* | 12/2004 | Kunz | A61B 17/00234 606/1 |
| 2005/0006429 A1 | 1/2005 | Wales et al. | |
| 2005/0006430 A1 | 1/2005 | Wales | |
| 2005/0006431 A1 | 1/2005 | Shelton et al. | |
| 2005/0006434 A1* | 1/2005 | Wales | A61B 17/07207 227/19 |
| 2005/0010235 A1 | 1/2005 | VanDusseldorp | |
| 2005/0023324 A1 | 2/2005 | Doll et al. | |
| 2005/0033299 A1 | 2/2005 | Shluzas | |
| 2005/0067458 A1 | 3/2005 | Swayze et al. | |
| 2005/0070925 A1 | 3/2005 | Shelton et al. | |
| 2005/0070958 A1 | 3/2005 | Swayze et al. | |
| 2005/0072827 A1 | 4/2005 | Mollenauer | |
| 2005/0131390 A1 | 6/2005 | Heinrich et al. | |
| 2005/0139636 A1 | 6/2005 | Schwemberger et al. | |
| 2005/0145674 A1 | 7/2005 | Sonnenschein et al. | |
| 2005/0171562 A1* | 8/2005 | Criscuolo | A61B 17/08 606/151 |
| 2005/0178813 A1* | 8/2005 | Swayze | A61B 17/07207 227/176.1 |
| 2005/0184123 A1* | 8/2005 | Scirica | A61B 17/07207 227/176.1 |
| 2005/0187576 A1 | 8/2005 | Whitman et al. | |
| 2005/1770176 | 8/2005 | Gerbi et al. | |
| 2005/0192609 A1 | 9/2005 | Whitman et al. | |
| 2005/0228341 A1 | 10/2005 | Edgerley | |
| 2005/0234297 A1 | 10/2005 | Devierre et al. | |
| 2005/0247753 A1 | 11/2005 | Kelly et al. | |
| 2005/0251175 A1* | 11/2005 | Weisenburgh | A61B 17/068 606/153 |
| 2006/0000867 A1 | 1/2006 | Shelton et al. | |

(56) References Cited

U.S. PATENT DOCUMENTS

| | | |
|---|---|---|
| 2006/0022014 A1 | 2/2006 | Shelton et al. |
| 2006/0022015 A1 | 2/2006 | Shelton et al. |
| 2006/0049229 A1 | 3/2006 | Milliman et al. |
| 2006/0089651 A1 | 4/2006 | Trudeau et al. |
| 2006/0094932 A1 | 5/2006 | Goldfarb et al. |
| 2006/0097025 A1 | 5/2006 | Milliman et al. |
| 2006/0151567 A1 | 7/2006 | Roy |
| 2006/0175375 A1* | 8/2006 | Shelton, IV ..... A61B 17/07207 227/176.1 |
| 2006/0212069 A1* | 9/2006 | Shelton, IV ..... A61B 17/07207 606/205 |
| 2006/0229633 A1 | 10/2006 | Shepherd |
| 2006/0278680 A1* | 12/2006 | Viola .................. A61B 17/072 227/176.1 |
| 2007/0023476 A1 | 2/2007 | Whitman et al. |
| 2007/0023477 A1* | 2/2007 | Whitman ............ A61B 17/068 227/175.1 |
| 2007/0027468 A1* | 2/2007 | Wales ................... A61B 90/03 606/205 |
| 2007/0029363 A1 | 2/2007 | Popov |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0083209 A1* | 4/2007 | Schenberger ........ A61B 17/142 606/82 |
| 2007/0084896 A1 | 4/2007 | Doll et al. |
| 2007/0084897 A1 | 4/2007 | Shelton et al. |
| 2007/0084899 A1* | 4/2007 | Taylor ............. A61B 17/07207 227/176.1 |
| 2007/0102472 A1 | 5/2007 | Shelton |
| 2007/0102473 A1 | 5/2007 | Shelton et al. |
| 2007/0102474 A1 | 5/2007 | Shelton et al. |
| 2007/0102475 A1 | 5/2007 | Ortiz et al. |
| 2007/0125826 A1 | 6/2007 | Shelton |
| 2007/0152014 A1 | 7/2007 | Gillum et al. |
| 2007/0158385 A1 | 7/2007 | Hueil et al. |
| 2007/0175947 A1 | 8/2007 | Ortiz et al. |
| 2007/0175949 A1 | 8/2007 | Shelton et al. |
| 2007/0175950 A1* | 8/2007 | Shelton, IV ..... A61B 17/07207 227/176.1 |
| 2007/0175951 A1 | 8/2007 | Shelton et al. |
| 2007/0175952 A1 | 8/2007 | Shelton et al. |
| 2007/0175953 A1 | 8/2007 | Shelton et al. |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175961 A1 | 8/2007 | Shelton et al. |
| 2007/0175962 A1 | 8/2007 | Shelton et al. |
| 2007/0175964 A1* | 8/2007 | Shelton .................. A61B 34/30 227/180.1 |
| 2007/0187453 A1 | 8/2007 | Smith et al. |
| 2007/0219563 A1 | 9/2007 | Voegele |
| 2007/0265640 A1 | 11/2007 | Kortenbach et al. |
| 2007/0278277 A1 | 12/2007 | Wixey et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0078801 A1* | 4/2008 | Shelton .................. A61B 17/072 227/175.1 |
| 2008/0110957 A1 | 5/2008 | McBride et al. |
| 2008/0135600 A1 | 6/2008 | Hiranuma et al. |
| 2008/0164296 A1 | 7/2008 | Shelton et al. |
| 2008/0169329 A1 | 7/2008 | Shelton et al. |
| 2008/0185419 A1 | 8/2008 | Smith et al. |
| 2008/0277449 A1 | 11/2008 | Marczyk |
| 2014/0343577 A1* | 11/2014 | Zemlok ............ A61B 17/00234 606/139 |
| 2017/0360436 A1* | 12/2017 | Zemlok ............ A61B 17/00234 |
| 2023/0038169 A1* | 2/2023 | Prema Mohanasundaram ............ A61B 17/07207 |

FOREIGN PATENT DOCUMENTS

| | | |
|---|---|---|
| EP | 0537570 B1 | 1/1998 |
| EP | 1563791 A1 | 8/2005 |
| EP | 1769754 A1 | 4/2007 |
| EP | 1813203 A2 | 8/2007 |
| EP | 1970015 A2 | 9/2008 |
| WO | 9518572 A1 | 7/1995 |
| WO | 9729694 A1 | 8/1997 |
| WO | 9740760 A1 | 11/1997 |
| WO | 99/952489 | 10/1999 |
| WO | 9952489 A1 | 10/1999 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007118179 A2 | 10/2007 |

OTHER PUBLICATIONS

International Search Report for corresponding PCT Application—PCT/US06121524—dated May 28, 2008 (4 Pages).

Detemple, P., "Microtechnology in Modem Health Care", Med Device Technol. 9(9):18-25 (1998).

European Search Report for corresponding EP 08252703.7 dated Oct. 31, 2008 (3 pages).

European Search Report dated Feb. 27, 2009 for Corresponding Patent Application 08253184.9.

European Search Report for corresponding EP 08252703.7 dated Oct. 31, 2008 (7 pages).

European Search Report for EP 08251351.6-2310 date of completion is Feb. 24, 2010 (3 pages).

European Search Report for Corresponding EP 08251357 dated Sep. 29. 2009 (3 pages).

European Search Report dated Jul. 28, 2011 for EP 11 15 2266.

European Search Report dated Apr. 17, 2007 for Corresponding EP Application EP 06026840.

European Search Report dated Feb. 27, 2009 for Corresponding EP Application 08253184.9.

Chinese Office Action corresponding to CN 2013102797095 dated Oct. 24, 2014; (11 pp).

Chinese Office Action corresponding to CN 201310279709.5 dated Jun. 26, 2015; 9 pp.

Extended European Search Report corresponding to counterpart Patent Application EP 18215973.1 dated Mar. 14, 2019.

European Office Action corresponding to counterpart Int'l Appln. No. EP 12 19 2850.1 dated Oct. 13, 2017.

U.S. H001904, Yates et al., Filed May 14, 1997.

U.S. H002037, Yates et al., Filed May 14, 1997.

Chinese First Office Action dated Aug. 11, 2011, issued in corresponding Chinese Appln. No. 200810090459, 4 pages.

Chinese Third Office Action dated Jan. 22, 2013, issued in corresponding Chinese Appln. No. 200810090459, 8 pages.

Australian Office Action dated May 25, 2012, issued in corresponding Australian Appln. No. 2008201492, 4 pages.

* cited by examiner

POWERED SURGICAL INSTRUMENT

CROSS-REFERENCE TO RELATED APPLICATIONS

The present application claims the benefit of, priority to, and is a Continuation application of U.S. patent application Ser. No. 17/064,638, filed on Oct. 7, 2020 (now U.S. Pat. No. 11,464,509), which is a Continuation of U.S. patent application Ser. No. 15/695,824, filed on Sep. 5, 2017 (now U.S. Pat. No. 10,799,238), which is a Continuation of U.S. patent application Ser. No. 14/452,782, filed on Aug. 6, 2014, which is a Continuation of U.S. patent application Ser. No. 11/786,933, filed on Apr. 13, 2007 (now U.S. Pat. No. 8,800,837), the entire content of each of which being incorporated by reference herein.

BACKGROUND

Technical Field

The present disclosure relates to surgical instruments for fastening body tissue and, more particularly, to a powered surgical instrument having powered actuation capabilities.

Surgical devices where tissue is first grasped or clamped between opposing jaw structure and then joined by surgical fasteners are well known in the art. In some instruments, a knife is provided to cut the tissue which has been joined by the fasteners. The fasteners typically include surgical staples and two part polymeric fasteners.

Instruments for this purpose may include two jaw members which are respectively used to capture or clamp tissue. Typically, one of the members carries a staple cartridge that houses a plurality of staples arranged in rows while the other member has an anvil that defines a surface for forming the staple legs as the staples are driven from the staple cartridge. Several instruments include clamps, handles and/or knobs to affect actuation along with rotation and articulation of an end effector. Such surgical instruments can require the user to exert a significant force in operating the handles, knobs, etc., which can create instability and undesired movement in operating the instruments.

Accordingly, surgical instruments that require less force to operate are desired. Surgical instruments that operate with more precision is also desired.

SUMMARY

The present disclosure relates to a surgical instrument including a housing, an endoscopic portion, a drive motor, a drive tube, a firing rod and an end effector. The endoscopic portion extends distally from the housing and defines a first longitudinal axis. The drive motor is disposed at least partially within the housing. The drive tube is disposed in mechanical cooperation with the drive motor and is rotatable about a drive tube axis extending therethrough. The firing rod is disposed in mechanical cooperation with the drive tube and at least a portion of the firing rod is translatable with respect to the drive tube. The end effector is disposed adjacent a distal portion of the endoscopic portion.

The present disclosure also relates to a method of applying surgical fasteners to tissue. The method of this embodiment includes providing a powered surgical instrument which includes a housing, an endoscopic portion, a drive motor, a drive tube, a firing rod and an end effector. The drive motor is disposed at least partially within the housing. The drive tube is disposed in mechanical cooperation with the drive motor and is rotatable about a drive tube axis extending therethrough. The firing rod is disposed in mechanical cooperation with the drive tube and at least a portion of the firing rod is translatable with respect to the drive tube. The end effector is disposed adjacent a distal portion of the endoscopic portion. The method further includes rotating the drive tube about the drive tube axis and translating the firing rod with respect to the drive tube to affect a surgical function of the end effector.

The present disclosure further relates to a surgical instrument comprising a housing, an endoscopic portion extending distally from the housing and defining a longitudinal axis, an end effector disposed adjacent a distal portion of the endoscopic portion, the end effector being movable to an angled position with respect to the longitudinal axis, a drive motor disposed at least partially within the housing, the drive motor being arranged for driving a surgical function of the end effector, an articulation mechanism for moving the end effector to the angled position with respect to the longitudinal axis, and an articulation motor for driving the articulation mechanism.

The surgical instrument may include a drive tube disposed in mechanical cooperation with the drive motor, the drive tube being rotatable about a drive tube axis extending therethrough, and a firing rod disposed in mechanical cooperation with the drive tube, at least a portion of the firing rod being translatable with respect to the drive tube. A clutch is disposed between the drive motor and the drive tube, in certain embodiments. The clutch may include a clutch plate and a spring. The clutch plate is desirably arranged to mate with an interface disposed on a proximal face of the drive tube. A manual articulation knob may also be included for driving the articulation mechanism.

The end effector is desirably rotatable about the longitudinal axis with respect to the housing, in certain embodiments. The surgical instrument desirably includes a user interface including at least one switch that controls the end effector. A power source is desirably disposed at least partially within the housing and arranged to provide power to the drive motor. In certain embodiments, the end effector is part of a disposable loading unit having a body portion.

DESCRIPTION OF THE DRAWINGS

Embodiments of the presently disclosed powered surgical instrument are disclosed herein with reference to the drawings, wherein.

DETAILED DESCRIPTION

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

Figure 1:
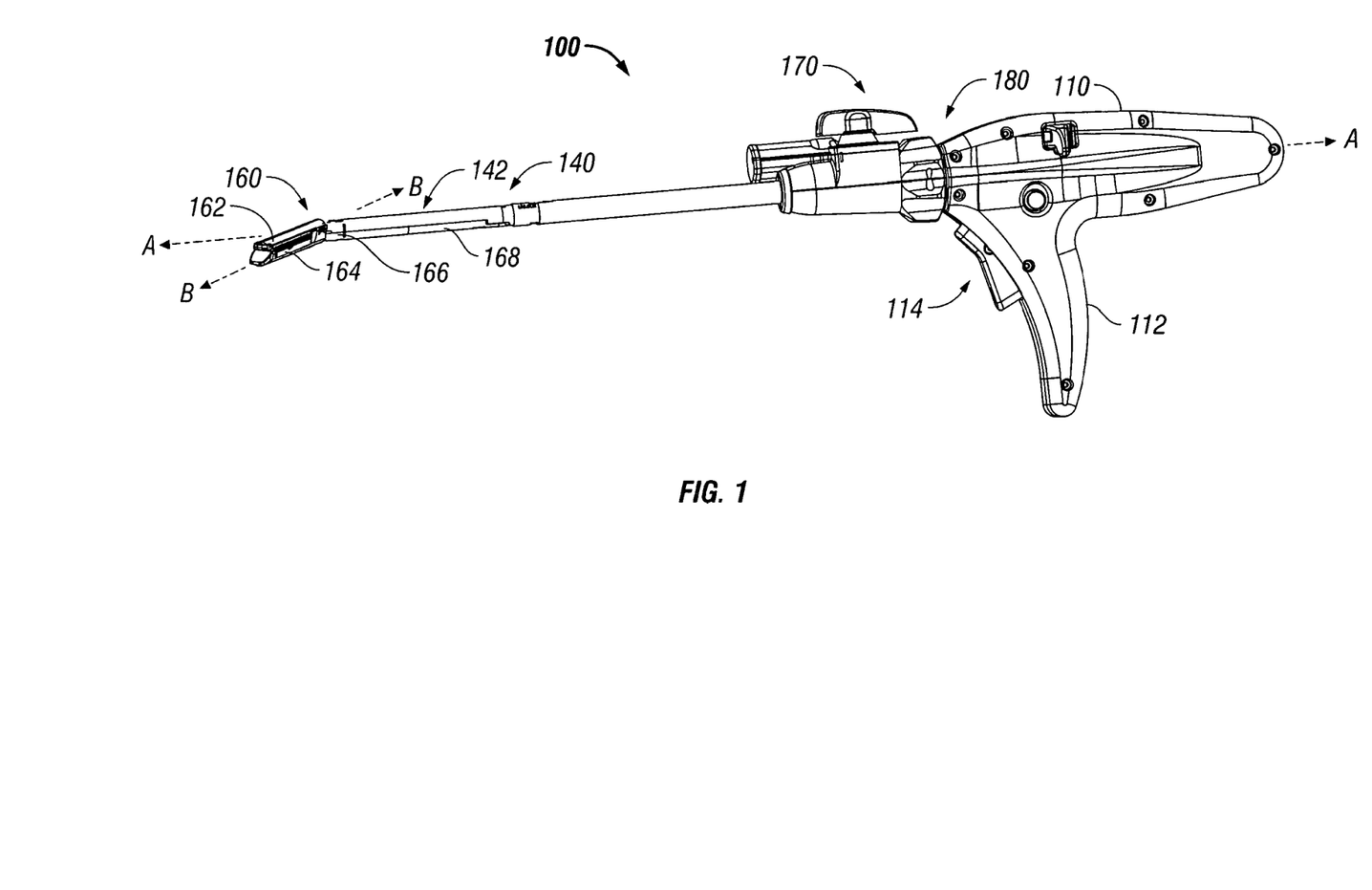
FIG. 1 is a perspective view of a powered surgical instrument according to an embodiment of the present disclosure.

A powered surgical instrument, e.g., a surgical stapler, in accordance with the present disclosure is referred to in the figures as reference numeral 100. Referring initially to FIG. 1, powered surgical instrument 100 includes a housing 110, an endoscopic portion 140 defining a first longitudinal axis A-A extending therethrough, and an end effector 160, defining a second longitudinal axis B-B extending therethrough. Endoscopic portion 140 extends distally from housing 110 and end effector 160 is disposed adjacent a distal portion 142 of endoscopic portion 140.

Figure 2:
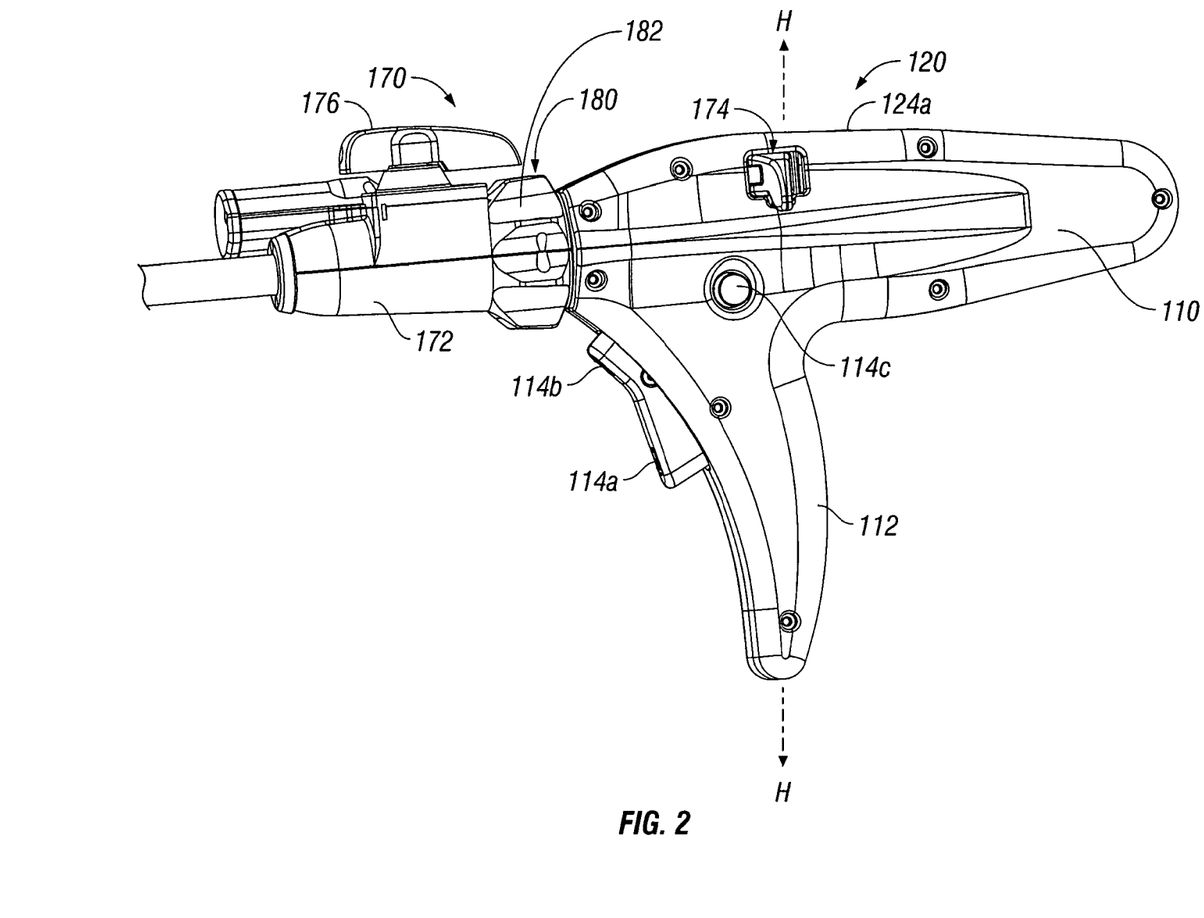
FIG. 2 is an enlarged partial perspective view of the powered surgical instrument of FIG. 1.

With reference to FIG. 2, an enlarged view of housing 110 is illustrated according to an embodiment of the present disclosure. In the illustrated embodiment, housing 110 includes a handle portion 112 having at least one switch 114 thereon (two switches 114*a* and 114*b* illustrated as a toggle switch are shown). Handle portion 112, which defines a handle axis H-H, is configured to be grasped by the hand of a user. Each switch 114*a* and 114*b* is shown as being disposed at a suitable location on handle portion 112 to facilitate its depression by a user's finger or fingers.

Figure 3:
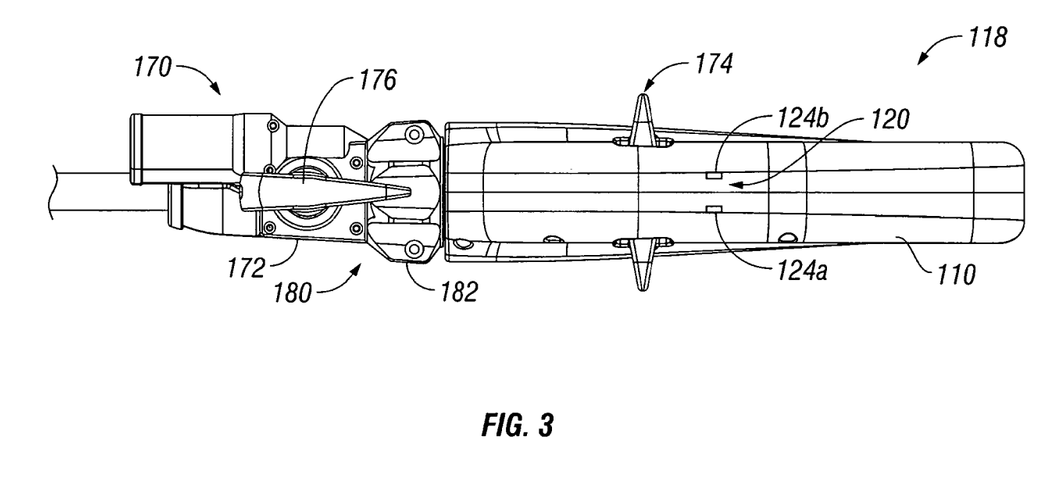
FIG. 3 is an enlarged plan view of the powered surgical instrument of FIGS. 1 and 2.

Referring to FIG. 3, a proximal area 118 of housing 110 includes a user interface 120. In the illustrated embodiment, user interface 120 includes two lights 124*a*, 124*b*. It is envisioned that lights 124*a*, 124*b* provide information/feedback (e.g., visual feedback) to its user. For example, illumination of first light 124*a* may indicate that a staple cartridge is loaded properly and illumination of second light 124*b* may indicate that second switch 114*b* (FIG. 2) has been initiated and that end effector 160 is ready to use. It is also envisioned that a screen (not explicitly shown in this embodiment) may be disposed on housing 110 to provide information/feedback to a user. The screen may comprise a LCD screen or other screen incorporated into housing 110.

Figure 4:
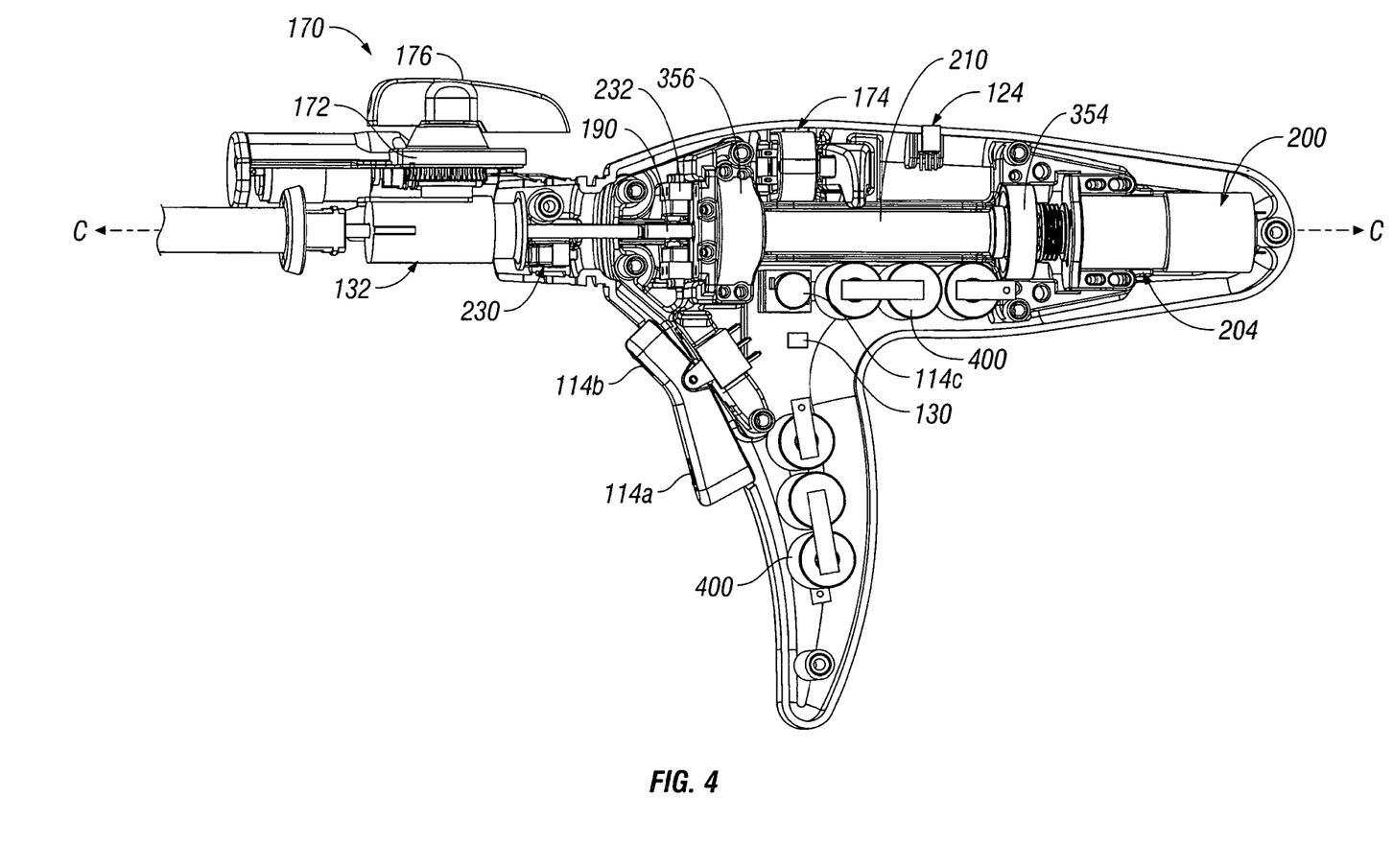
FIG. 4 is a partial perspective sectional view of the powered surgical instrument of FIGS. 1-3.

FIGS. 2-4 illustrate an articulation mechanism 170, including an articulation housing 172, a powered articulation switch 174 and a manual articulation knob 176. The knob 176 is desirably configured to indicate the angle of the end effector 160. For example, the angular displacement of the knob 176, which has an elongated shape, with respect to axis A-A indicates the angle of the end effector with respect to axis A-A. Actuation of articulation mechanism 170 (e.g., translating powered articulation switch 174 or pivoting manual articulation knob 176) causes end effector 160 to move from its first position, where longitudinal axis B-B is substantially aligned with longitudinal axis A-A, towards a position in which longitudinal axis B-B is disposed at an angle to longitudinal axis A-A. Preferably, a plurality of articulated positions is achieved.

Additionally, articulation housing 172 and powered articulation switch 174 are mounted to a rotating housing assembly 180. Rotation of a rotation knob 182 about first longitudinal axis A-A causes housing assembly 180 as well as articulation housing 172 and powered articulation switch 174 to rotate about first longitudinal axis A-A, and thus causes corresponding rotation of distal portion 224 of firing rod 220 and end effector 160 about first longitudinal axis A-A. Further details of articulation housing 172, powered articulation switch 174, manual articulation knob 176 and providing articulation to end effector 160 are described in U.S. Pat. Nos. 7,431,188 and 6,953,139, the contents of both of which are hereby incorporated by reference in their entirety. It is envisioned that any combinations of limit switches, proximity sensors (e.g., optical and/or ferromagnetic), linear variable displacement transducers and shaft encoders (disposed within housing 110, for instance) may be utilized to control and/or record an articulation angle of end effector 160 and/or position of firing rod 220.

FIGS. 4-8 illustrate various internal components of powered surgical instrument 100, including a drive motor 200 (FIG. 4), a drive tube 210 (FIGS. 4-7) and a firing rod 220 (including proximal portion 222 (FIGS. 5, 6 and 8) and distal portion 224 (FIGS. 4 and 5)). Drive tube 210 is rotatable about drive tube axis C-C extending therethrough (FIG. 4). Drive motor 200 is disposed in mechanical cooperation with drive tube 210 and is configured to rotate drive tube 210 about drive gear axis C-C. In a disclosed embodiment, drive motor 200 may be a motor or a gear motor, which may include gearing incorporated within its housing.

Figure 5:
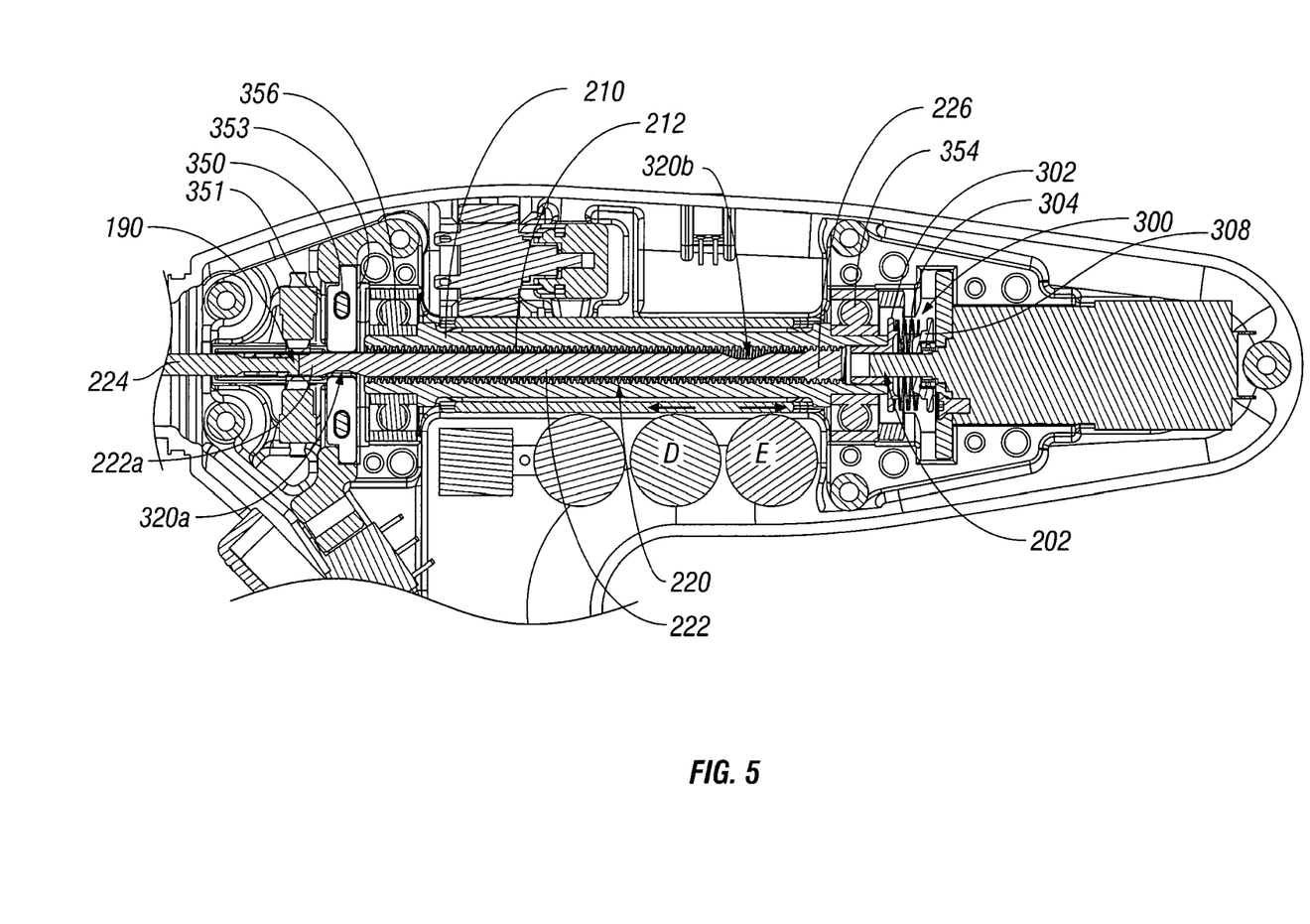
FIG. 5 is a cross-sectional view showing internal components of the powered surgical instrument of FIGS. 1-4 disposed in a first position.
Figure 6:
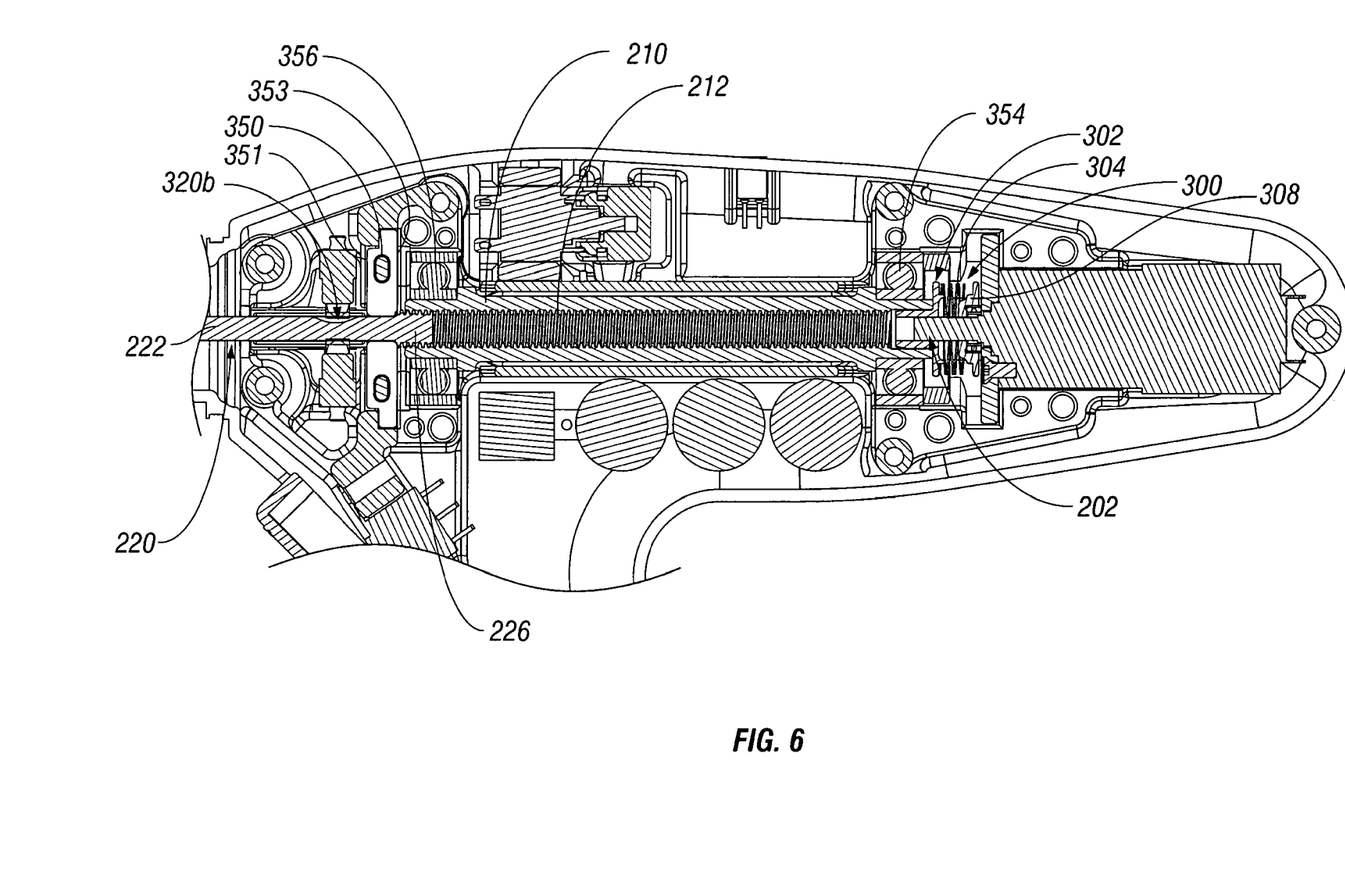
FIG. 6 is a cross-sectional view showing internal components of the powered surgical instrument of FIGS. 1-5 disposed in a second position.

With reference to FIGS. 4-6, a firing rod coupling 190 is illustrated. Firing rod coupling 190 provides a link between proximal portion 222 and distal portion 224 of firing rod 220. Specifically, firing rod coupling 190 enables rotation of distal portion 224 of firing rod 220 with respect to proximal portion 222 of firing rod 220. Thus, firing rod coupling 190 enables proximal portion 222 of firing rod 220 to remain stationary (discussed below with reference to alignment plate 350), while allowing rotation of distal portion 224 of firing rod 220 (e.g., upon rotation of rotation knob 182, discussed above).

Drive tube 210 rotates in response to rotation of drive motor 200. As drive tube 210 rotates, firing rod 220 is translated proximally and/or distally, as described below. With reference to FIGS. 5 and 6, proximal portion 222 of firing rod 220 includes a threaded portion 226, which extends through an internally-threaded portion 212 of drive tube 210. This relationship between firing rod 220 and drive tube 210 causes firing rod 220 to move distally and/or proximally (in the directions of arrows D and E) along threaded portion 212 of drive tube 210 upon rotation of drive tube 210. For example, as drive tube 210 rotates in a first direction (e.g., clockwise), firing rod 220 moves proximally (FIG. 5 illustrates firing rod 220 disposed adjacent its proximal-most position), and as drive tube 210 rotates in a second direction (e.g., counter-clockwise), firing rod 220 moves distally (FIG. 6 illustrates firing rod 220 adjacent its distal-most position).

With continued reference to FIGS. 5 and 6, firing rod 220 is distally and proximally translatable within particular limits. Specifically, a first end 222*a* of proximal portion 222 of firing rod 220 acts as a mechanical stop in combination with an alignment plate 350. That is, upon retraction when firing rod 220 is translated proximally, first end 222*a* contacts a distal surface 351 of alignment plate 350, thus preventing continued proximal translation of firing rod 220 (FIG. 5). Additionally, threaded portion 226 of proximal portion 222 of firing rod 220 acts as a mechanical stop in combination with alignment plate 350. That is, when firing rod 220 is translated distally, threaded portion 226 contacts a proximal surface 353 of alignment plate 350, thus preventing further distal translation of firing rod 220 (FIG. 6).

Figure 7:
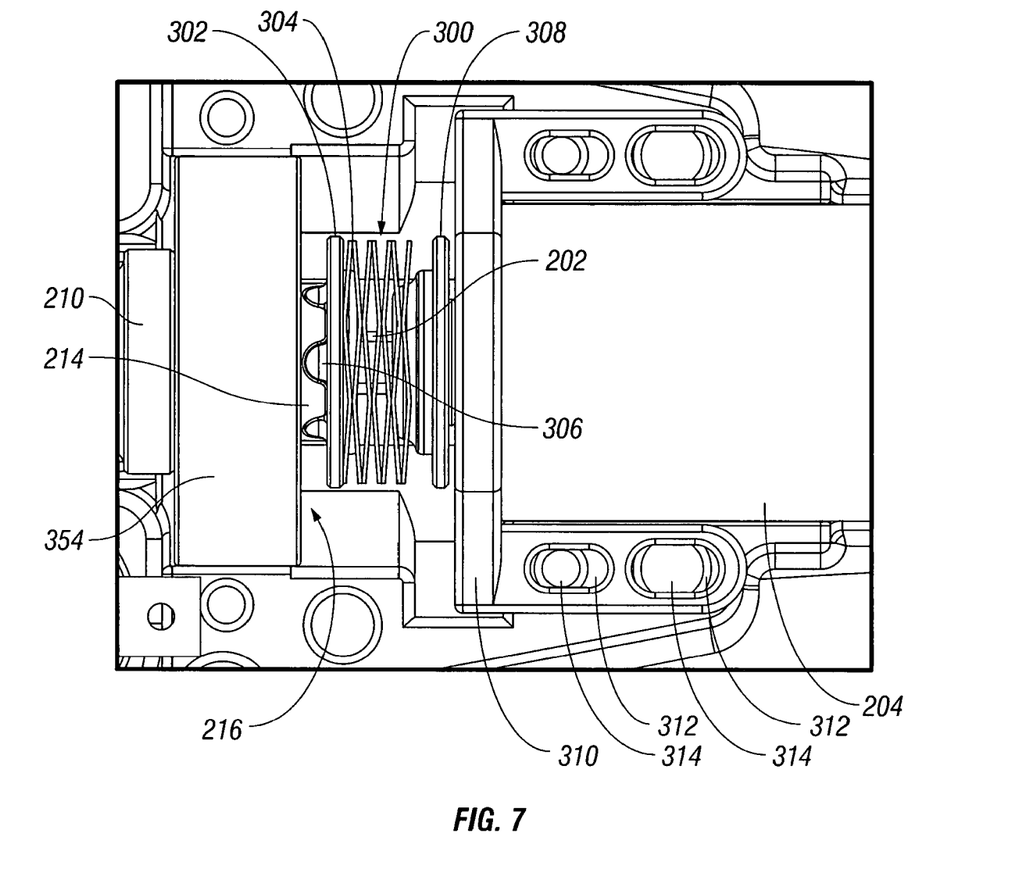
FIG. 7 is a partial cross-sectional view showing internal components of the powered surgical instrument of FIGS. 1-6.
Figure 8:
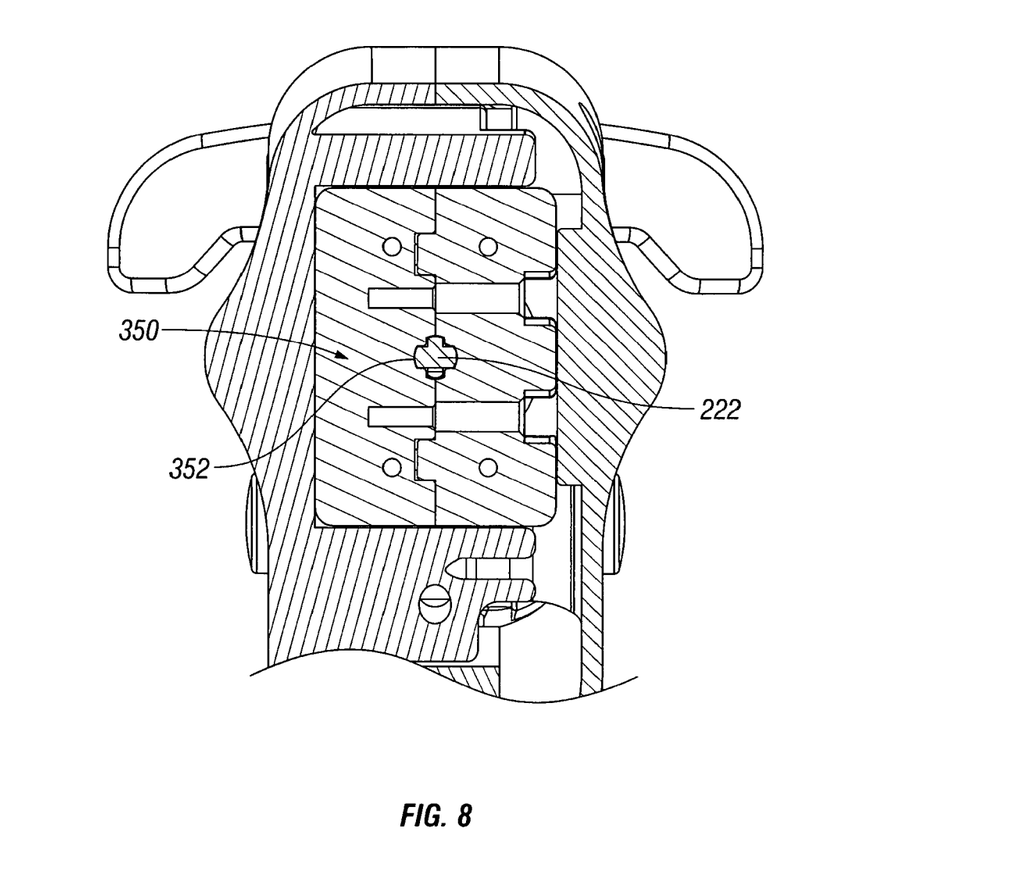
FIG. 8 is a cut-away view of a portion of the powered surgical instrument of FIGS. 1-7.

As drive tube 210 is rotated by drive motor 200, proximal portion 222 of firing rod 220 is constricted from substantial rotation by alignment plate 350 (FIG. 8). Alignment plate 350 includes an aperture 352 therethrough, which has a non-round cross-section. The non-round cross-section of aperture 352 prevents rotation of proximal portion 222 of firing rod 220, thus limiting proximal portion 222 of firing rod 220 to axial translation therethrough. Further, a proximal bearing 354 (FIGS. 4-7) and a distal bearing 356 (FIGS. 4-6) are disposed at least partially around drive tube 210 for facilitation of rotation of drive tube 210, while helping align drive tube 210 within housing 110. In further embodiments, additional tubes may be added. To reduce the length of the drive tube and/or increase the torque, the drive tube can incorporate an external thread which mates with another tubular member. This allows the telescoping, multi-layered tube to travel axially so that the firing rod will travel more axially, while the assembly has the same overall length. Furthermore, inner threaded tubes can also be utilized in a similar manner.

Distal translation of firing rod 220 (corresponding with a counter-clockwise rotation of drive tube 210, for instance) can cause jaw members 162, 164 (see FIG. 1) of end effector 160 to grasp or clamp tissue held therebetween. Additional distal translation of firing rod 220 may cause surgical fasteners to be ejected from end effector 160 (e.g., via cam bars and/or an actuation sled (neither of which are explicitly shown in this embodiment)) to fasten tissue and may also cause a knife (not explicitly shown in this embodiment) to sever tissue. Proximal translation of firing rod 220 (corresponding with a clockwise rotation of drive tube 210, for instance) can cause jaw members 162, 164 and/or knife to retract or return to their pre-fired positions. Further details of firing and otherwise actuating end effector 160 are described in U.S. Pat. No. 6,953,139 to Milliman et al. (the '139 Milliman patent), the disclosure of which is hereby incorporated by reference herein in its entirety.

According to an embodiment of the present disclosure, end effector 160 includes a cartridge assembly (e.g., jaw member 164) and an anvil assembly (e.g., jaw member 162) including an anvil portion for deploying surgical fasteners into body tissue and forming the surgical fasteners. Cartridge assembly 164 houses a plurality of staples. At least one of anvil assembly 162 and cartridge assembly 164 is movable in relation to one another between an open position where anvil assembly 162 is spaced from cartridge assembly 164 and an approximated or clamped position where anvil assembly 162 is in juxtaposed alignment with cartridge assembly 164. In an embodiment, the staples are housed in cartridge assembly 164 to apply linear rows of staples to body tissue.

It is further envisioned that end effector 160 is attached to a mounting portion 166, which is pivotably attached to a body portion 168. Body portion 168 may be integral with endoscopic portion 140 of powered surgical instrument 100, or may be removably attached thereto to provide a replaceable, disposable loading unit (DLU) or single use loading unit (SULU). The loading unit may be connectable to endoscopic portion 140 through a bayonet connection. It is envisioned that the loading unit has at least one articulation link connected to mounting portion 166 of the loading unit and the articulation link is connected to a linkage rod so that the end effector 160 is articulated as the linkage rod is translated in the distal-proximal direction along first longitudinal axis A-A. Other means of connecting end effector 160 to endoscopic portion 140 to allow articulation may be used. For example, a flexible tube or a plurality of pivotable members may be used.

A loading unit may incorporate (or be configured to incorporate) various end effectors, such as vessel sealing devices, linear stapling devices, circular stapling devices, cutters, etc. Such end effectors may be coupled to endoscopic portion 140 of powered surgical instrument 100. An intermediate flexible shaft may be included between handle portion 112 and loading unit. An example of a flexible shaft is described in U.S. Pat. No. 7,950,560, the contents of which are hereby incorporated by reference in their entirety. It is envisioned that the incorporation of a flexible shaft may facilitate access to and/or within certain areas of the body.

Further, where various loading units can be used, a digital control module (DCM) 130 (FIG. 4) can control the force being applied to firing rod 220 so that firing rod 220 can drive the particular end effector 160 that is on the loading unit in use at the time. For clarity, wires are not shown in the Figures connecting DCM 130 to various components of powered surgical instrument 100, but such wires are contemplated by the present disclosure. The loading unit may also include a mechanical or electronic sensor, e.g., 132, that indicates to DCM 130 which end effector is on the loading unit. In an embodiment, DCM 130 is also capable of storing information relating to the force applied to firing rod 220 and/or end effector 160 via sensors or by measuring the voltage and current being drawn by the motor. Additionally, the voltage and current from drive motor 200 may be measured to provide information and/or feedback regarding the state of powered surgical instrument 100. For instance, if the user is attempting to clamp down on tissue that is too thick, the voltage and/or current can be measured to determine the clamping energy. If predetermined energy limitations are exceeded, this information can be provided to the user and/or the power can be interrupted or ceased. It is envisioned that such a feature helps prevent damage to the mechanisms in the instrument.

In an embodiment of the disclosure, anvil assembly 162 of end effector 160 includes a cam surface for being engaged by a drive assembly of end effector 160. Here, the drive assembly includes a drive beam, which desirably has a knife for cutting tissue. The drive beam has a cam roller positioned to engage the cam surface, and a flange positioned to engage the cartridge assembly to affect approximation of the anvil assembly 162 and cartridge assembly 164 with respect to one another when the drive beam is advanced distally. In addition, when advanced further in the distal direction, the drive beam engages an actuation member for deploying the surgical fasteners from the cartridge assembly, as disclosed in the Milliman '139 patent.

Any combination of sensors may be positioned within powered surgical instrument 100 to determine its operating stage, e.g., articulation, rotation, clamping, firing of end effector 160, etc. For example, limit switches 230 and 232 (FIG. 4), proximity sensors (e.g., linear and/or ferromagnetic), potentiometers, linear variable displacement transducers (LVDT), shaft encoders, etc., may be used to help control and/or record the location of firing rod 220 (e.g., limit switch 232) and may be used to detect a properly loaded staple cartridge (e.g., limit switch 230).

With reference to FIGS. 5 and 6, indicators 320a, 320b are illustrated on firing rod 220 and help determine the speed of firing rod 220 and the location of firing rod 220 with respect to drive tube 210 and/or housing 110. For instance, limit switch 230 may be activated by sensing indicators 320a and/or 320b (e.g., bumps, grooves, indentations, etc.) passing thereby to determine position of firing rod 220, speed of firing rod 220 and mode of powered surgical instrument 100 (e.g., clamping, grasping, firing, sealing, cutting, retracting). The indicators may have a variety of shapes and many equally spaced features similar to those shown can be used. The position of firing rod 220, for example, may be indicated on a screen of user interface 120. Further, the feedback received from indicators 320a, 320b may be used to determine when firing rod 220 should stop its axial movement (e.g., when drive motor 200 should cease) depending on the size of the particular loading unit attached thereto.

With reference to FIG. 7, a drive motor shaft 202 is shown extending from drive motor 200 and a planetary gear 204. Drive motor shaft 202 is in mechanical cooperation with clutch 300. Drive motor shaft 202 is rotated by drive motor 200, thus resulting in rotation of clutch 300. Clutch 300 includes a clutch plate 302 and a spring 304 and is shown having wedged portions 306 disposed on clutch plate 302, which are matable with an interface (e.g., wedges 214) disposed on a proximal face 216 of drive tube 210. Spring 304 is illustrated between planetary gear 204 and drive tube 210. Specifically, and in accordance with the embodiment illustrated in FIG. 7, spring 304 is illustrated between clutch plate 302 and a clutch washer 308. Additionally, drive motor 200 is mounted on a motor mount 310. As illustrated in FIG. 7, motor mount 310 is adjustable proximally and distally with respect to housing 110 via slots 312 disposed in motor mount 310 and protrusions 314 disposed on housing 110.

In an embodiment of the disclosure, a clutch is formed between the drive tube 210 and the drive motor 200. Wedged portions 306 of clutch 300 are configured and arranged to slip with respect to wedges 214 of proximal face 216 of drive tube 210 unless a threshold force is applied to clutch plate 302 clutch spring 304. Further, when spring 304 applies the threshold force needed for wedged portions 306 and wedges 214 to engage without slipping, drive tube 210 will rotate upon rotation of drive motor 200. It is envisioned that wedged portions 306 and/or wedges 214 are configured to slip in one and/or both directions (i.e., clockwise and/or counter-clockwise) with respect to one another until a threshold force is attained.

It is further envisioned that drive motor shaft 202 includes a D-shaped cross-section, which includes a substantially flat portion and a rounded portion. Thus, while drive motor shaft 202 is translatable with respect to clutch plate 302, drive motor shaft 202 will not "slip" with respect to clutch plate 302 upon rotation of drive motor shaft 202. That is, rotation of drive motor shaft 202 will result in a relatively slip-less rotation of clutch plate 302.

While not explicitly illustrated in the accompanying figures, user interface 120 may include a plurality of switches. User interface may display the "mode" (e.g., rotation, articulation or actuation), which may be communicated to user interface via a sensor, "status" (e.g., angle of articulation, speed of rotation, or type of actuation) and "feedback," such as whether staples have been fired. It is also envisioned that switch can be used to let a user input different tissue types, and various sizes and lengths of staple cartridges. Further, switches on user interface may include arrows thereon and may be used for selecting the direction, speed and/or torque at which drive tube 210 is rotated by drive motor 200. It is also envisioned that at least one switch can be used for selecting an emergency mode that overrides various settings, for example.

Additionally, and with reference to FIGS. 1 and 2, switches 114a, 114b may be used for starting and/or stopping movement of drive motor 200. Other functions for switches 114a, 114b are also anticipated as well as having more or fewer switches 114. In a particular embodiment, a switch 114c may be included (FIGS. 1, 2 and 4), wherein depression thereof may mechanically and/or electrically initiate actuation or firing of end effector 160. Further, at least one switch 114 may include one or more microelectronic membrane switches, for example. Such a microelectronic membrane switch includes a relatively low actuation force, small package size, ergonomic size and shape, low profile, the ability to include molded letters on the switch, symbols, depictions and/or indications, and a low material cost. Additionally, switches 114 (such as microelectronic membrane switches) may be sealed to help facilitate sterilization of powered surgical instrument 100, as well as helping to prevent particle and/or fluid contamination.

As an alternative to, or in addition to switches 114, other input devices may include voice input technology, which may include hardware and/or software incorporated in DCM 130, or a separate digital module connected to DCM 130. The voice input technology may include voice recognition, voice activation, voice rectification and/or embedded speech. The user may be able to control the operation of the instrument in whole or in part through voice commands, thus freeing one or both of the user's hands for operating other instruments. Voice or other audible output may also be used to provide the user with feedback.

In an embodiment, spring 304 may be used in the feedback and control of powered surgical instrument 100. As described above, DCM 130 may be connected to one or more switches 114 and one or more display screens to provide feedback to the user and for helping to control the operation of powered surgical instrument 100. DCM 130 may be a digital board incorporated in housing 110 of powered surgical instrument 100. Spring 304 may include a pressure transducer that can interact with DCM 130 to control the force being applied to drive tube 210.

It is also envisioned that user interface 120 includes different colors and/or intensities of text on screen and/or on switches for further differentiation between the displayed items. User feedback can also be included in the form of pulsed patterns of light, acoustic feedback (e.g., buzzers, bells or beeps that may be sounded at selected time intervals), verbal feedback, and/or haptic vibratory feedback (such as an asynchronous motor or solenoids), for example. The visual, auditory or haptic feedback can be increased or decreased in intensity. For example, the intensity of the feedback may be used to indicate that the forces on the instrument are becoming excessive. Additionally, switches may be positioned at different heights from one another and/or may include raised indicia or other textural features (e.g., concavity or convexity) to allow a user to depress an appropriate switch without the need to look at user interface 120.

Additionally, user interface 120 may include a separate display screen or screens and input devices (such as switches or buttons), or the input devices may be incorporated in whole or in part in screen. For example, a touch screen liquid crystal display (LCD) may be used to allow the user to provide input while viewing operational feedback. The touch screen LCD may include resistive, capacitive or surface acoustic wave controls. This approach may enable facilitation of sealing screen components to help sterilize powered surgical instrument 100, as well as preventing particle and/or fluid contamination. In certain embodiments, screen is pivotably or rotatably mounted to powered surgical instrument 100 for flexibility in viewing screen during use or preparation. Screen may be hinged or ball-and-socket mounted to powered surgical instrument 100, for example.

In a disclosed embodiment, at least some of the information monitored by the various sensors in powered surgical instrument 100 may be provided to a video screen or monitoring system in an operating room. For instance, the data may be transmitted to a receiver for the operating room monitoring system from a communication transmitter incorporated in or associated with powered surgical instrument 100, via technology including Blue Tooth, ANT3, KNX, Z Wave, X10, wireless USB, WiFi, IrDa, Nanonet, Tiny OS, ZigBee, radio frequency, UHF and VHF. Such features may facilitate monitoring by the user of powered surgical instrument 100 or other operating room or hospital personnel or remotely located persons.

It is also envisioned that any combination of battery cells 400 (FIG. 4), a battery pack, fuel cell and/or high-energy capacitor may be used to provide power to powered surgical instrument 100. For example, capacitors may be used in conjunction with a battery pack. Here, capacitors can be used for a burst of power when energy is desired/required more quickly than can be provided with a battery on its own (e.g., when clamping thick tissue, rapid firing, clamping, etc.), as batteries are typically slow-drain devices from which current cannot be quickly drawn. It is envisioned that batteries can be connected to capacitors to charge the capacitors.

It is also envisioned that battery pack includes at least one disposable battery. The disposable battery may be between about 9 volts and about 30 volts and may be useful in a disposable surgical instrument. Other power-supplying means are also contemplated including electric power. In alternative embodiments a cord is provided to connect instrument 100 to a generator and/or line voltage.

In a disclosed embodiment, the DCM is connected to drive motor 200 and is configured and arranged to monitor the battery impedance, voltage, temperature and/or current draw and to control the operation of powered surgical instrument 100. The load or loads on battery 400, transmission, drive motor 200 and drive components of powered surgical instrument 100 are determined to control a motor speed if the load or loads indicate a damaging limitation is reached or approached. For example, the energy remaining in battery 400, the number of firings remaining, whether battery 400 must be replaced or charged, and/or approaching the potential loading limits of powered surgical instrument 100 may be determined.

The DCM can be configured and arranged to control or help control the operation of drive motor 200 to respond to the monitored information. Pulse modulation of the battery voltage can be used as an electronic clutch for controlling the torque output. For example, the DCM can regulate the voltage or pulse modulate the voltage to adjust the power and/or torque output to prevent system damage or optimize energy usage. An electric braking circuit may be used for controlling drive motor 200, which uses the existing back electromotive force (EMF) of rotating drive motor 200 to counteract and substantially reduce the momentum of drive tube 210. The electric braking circuit may improve the control of drive motor 200 and/or drive tube 210 for stopping accuracy and/or shift location of powered surgical instrument 100. Sensors for monitoring components of powered surgical instrument 100 and to help prevent overloading of powered surgical instrument 100 may include thermal-type sensors, such as thermal sensors, thermistors, thermopiles, thermo-couples and/or thermal infrared imaging and provide feedback to the DCM. The DCM may control the components of powered surgical instrument 100 in the event that limits are reached or approached and such control can include cutting off the power from the battery pack 400, temporarily interrupting the power or going into a pause mode, pulse modulation to limit the energy used, and the DCM can monitor the temperature of components to determine when operation can be resumed. The above uses of the DCM may be used independently of or factored with current, voltage, temperature and/or impedance measurements.

It is envisioned that end effector 160 is reusable, can accept a staple cartridge and/or is part of a disposable loading unit. Further details of a disposable or replaceable loading unit are described in U.S. Pat. No. 5,752,644 to Bolanos et al., the entire contents of which are hereby incorporated by reference herein. Disposable and/or replaceable loading units can include end effectors with or without articulation, as disclosed in the '139 Milliman patent.

A disposable or replaceable loading unit incorporating a surgical end effector 160, in certain embodiments of the present disclosure, includes sensors positioned within the loading unit to determine the position of various components and/or operation of end effector 160, such as articulation, rotation, clamping and firing of end effector 160. For example, electrical contacts, proximity sensors, optical sensors, photo diodes, and/or mechanical or metallic sensors may be used to control and/or record information concerning the end effector 160. The location of the anvil assembly 162 and cartridge assembly 164 with respect to one another, the articulated or non-articulated position of end effector 160, rotation of end effector 160, and/or correct loading of the loading unit, staple cartridge and/or components of the staple cartridge may also be determined.

An identification system may also be included to determine and communicate to the DCM various information, including the speed, power, torque, clamping, travel length and strength limitations for operating the particular end effector 160. The DCM may also determine the operational mode and adjust the voltage, clutch spring loading and stop points for travel of the components. More specifically, the identification system may include a component (e.g., a microchip, emitter or transmitter) in end effector 160 that communicates (e.g., wirelessly, via infrared signals, etc.) with the DCM, or a receiver therein. It is also envisioned that a signal may be sent via firing rod 220, such that firing rod 220 functions as a conduit for communications between the DCM and end effector 160.

The loading unit, in certain embodiments according to the present disclosure, includes an axial drive assembly that cooperates with firing rod 220 to approximate anvil assembly 162 and cartridge assembly 164 of end effector 160, and fire staples from the staple cartridge. The axial drive assembly may include a beam that travels distally through the staple cartridge and may be retracted after the staples have been fired, as disclosed in certain embodiments of the '139 Milliman patent. By way of example, the sensors discussed above may be used to determine if the staples have been fired from the staple cartridge, whether they have been fully fired, whether and the extent to which the beam has been retracted proximally through the staple cartridge and other information regarding the operation of the loading unit. In certain embodiments of the present disclosure, the loading unit incorporates components for identifying the type of loading unit, and/or staple cartridge loaded on the instrument 100, including infra red, cellular, conductive identification (which may utilize the firing rod as a conduit) or radio frequency identification chips (such as Sensormatic or similar technology). The type of loading unit and/or staple cartridge may be received by an associated receiver within the DCM, or an external device in the operating room for providing feedback, control and/or inventory analysis. The power or battery pack 400 can incorporate a component for identifying the type of power pack 400 loaded with powered surgical instrument 100 or for sending feedback concerning the status of power pack 400.

In certain embodiments of the present disclosure, powered surgical instrument 100 includes disposable or replaceable loading units incorporating a surgical end effector 160 and a reusable portion including a housing 110 and endoscopic portion 140 that is removably attached to the loading unit. The reusable portion may be configured for sterilization and re-use in a subsequent surgical procedure. In an embodiment, the components of the housing 110 are sealed against infiltration of particulate and/or fluid contamination and help prevent damage of the component by the sterilization process. Power pack 400, in certain embodiments according to the present disclosure, comprises a rechargeable battery. The rechargeable battery can be connected to contacts accessible at housing 110 of the instrument 100, for example, or, rechargeable battery may be rechargeable through an inductive charging interface sealed within housing 110. The inductive charging interface may eliminate shorting of contacts and provides an internal battery that may be hermetically or liquid resistance sealed.

The present disclosure also relates to a method of applying surgical fasteners to tissue. The method includes the use of powered surgical instrument 100, as described above.

It will be understood that various modifications may be made to the embodiments disclosed herein. Sensors, feedback and control systems are desirably incorporated into the surgical instrument, in certain preferred embodiments, as disclosed above and as disclosed in U.S. Pat. No. 7,950,560, the disclosure of which is hereby incorporated by reference herein in its entirety.

As a further example, a movable handle (not explicitly shown in this embodiment) may be employed to control various functions of powered surgical instrument 100. Therefore, the above description should not be construed as limiting, but merely as exemplifications of various embodiments. Those skilled in the art will envision other modifications within the scope and spirit of the claims appended hereto.

What is claimed is:

1. A surgical instrument, comprising:
a housing;
a first firing rod disposed in mechanical cooperation with the housing, at least a portion of the first firing rod being movable relative to the housing;
a second firing rod; and
a coupling interconnecting the first firing rod and the second firing rod, the coupling configured to allow rotation of the second firing rod relative to the first firing rod.

2. The surgical instrument according to claim 1, further including an elongated portion extending distally from the housing and defining a first longitudinal axis.

3. The surgical instrument according to claim 2, wherein the coupling is coaxial with the first longitudinal axis.

4. The surgical instrument according to claim 2, wherein the first firing rod and the second firing rod are disposed along the first longitudinal axis.

5. The surgical instrument according to claim 1, further including at least one sensor and at least two indicators, wherein the at least one sensor is configured to sense the at least two indicators to determine at least one of a speed at which the first firing rod is moving relative to the housing or a position of the first firing rod relative to the housing.

6. The surgical instrument according to claim 5, wherein the at least two indicators are disposed on the first firing rod.

7. The surgical instrument according to claim 1, further including an end effector disposed in mechanical cooperation with the second firing rod such that rotation of the second firing rod relative to the housing drives a surgical function of the end effector.

8. The surgical instrument according to claim 7, further including an elongated portion extending distally from the housing and defining a first longitudinal axis, wherein the end effector is rotatable about the first longitudinal axis relative to the housing.

9. The surgical instrument according to claim 1, further including a user interface having at least one switch that controls movement of the first firing rod relative to the housing.

10. The surgical instrument according to claim 1, wherein at least a portion of the first firing rod extends through an aperture of a plate.

11. The surgical instrument according to claim 10, wherein the aperture includes a non-round cross-section for preventing rotation of the first firing rod relative to the plate.

12. The surgical instrument according to claim 1, wherein the first firing rod is disposed proximally of at least a majority of the second firing rod.

13. The surgical instrument according to claim 1, wherein the coupling is fixed from longitudinal movement relative to the housing.

14. A surgical instrument, comprising:
a housing;
a rod disposed in mechanical cooperation with the housing, at least a portion of the rod being translatable relative to the housing;
at least one sensor; and
at least two indicators, wherein the at least one sensor is configured to sense the at least two indicators to determine at least one of a speed at which the rod is moving relative to the housing or a position of the rod relative to the housing.

15. The surgical instrument according to claim 14, wherein the at least one sensor or the at least two indicators are disposed on the rod.

16. The surgical instrument according to claim 14, further comprising a limit switch disposed in mechanical cooperation with the housing, wherein the limit switch is activated when the at least two indicators are moved into a predetermined position.

17. The surgical instrument according to claim 14, wherein a portion of the rod is rotatable relative to the housing, and wherein a portion of the rod is not rotatable relative to the housing.

18. The surgical instrument according to claim 17, further including an elongated portion extending distally from the housing and defining a first longitudinal axis, wherein the portion of the rod that is rotatable relative to the housing is disposed along the longitudinal axis, and wherein the portion of the rod that is not rotatable relative to the housing is disposed along the longitudinal axis.

19. The surgical instrument according to claim 17, wherein the at least two indicators are disposed on the portion of the rod that is non-rotatable relative to the housing.

20. The surgical instrument according to claim 14, further including a drive motor disposed at least partially within the housing, and a drive tube disposed in mechanical cooperation with the drive motor, the drive tube being rotatable about a drive tube axis extending therethrough.

\* \* \* \* \*